(12) United States Patent
Helenberger et al.

(10) Patent No.: US 7,083,654 B2
(45) Date of Patent: Aug. 1, 2006

(54) PROSTHETIC ANGLED LOCKING COUPLER DEVICE

(75) Inventors: Derek M. Helenberger, Berkley, MI (US); Wendy Beattie, Bloomfield Hills, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

(21) Appl. No.: 10/642,047

(22) Filed: Aug. 15, 2003

(65) Prior Publication Data
US 2005/0038522 A1   Feb. 17, 2005

(51) Int. Cl.
*A61F 2/60*   (2006.01)
*A61F 2/78*   (2006.01)

(52) U.S. Cl. .......................................... 623/33; 623/36
(58) Field of Classification Search .................. 623/38, 623/27, 33, 36, 39, 34, 35
See application file for complete search history.

(56) References Cited

U.S. PATENT DOCUMENTS

| | | | |
|---|---|---|---|
| 5,226,918 A * | 7/1993 | Silagy et al. ................. | 623/32 |
| 5,507,837 A | 4/1996 | Laghi | |
| 5,888,234 A | 3/1999 | Littig | |
| 6,051,026 A | 4/2000 | Biedermann et al. | |
| 6,106,559 A * | 8/2000 | Meyer .......................... | 623/33 |
| 6,267,787 B1 * | 7/2001 | Capper et al. ................. | 623/36 |
| 6,589,289 B1 * | 7/2003 | Ingimarsson .................. | 623/33 |
| 6,689,171 B1 * | 2/2004 | Slemker et al. ................ | 623/33 |
| 2002/0193887 A1 * | 12/2002 | Swanson, Sr. ................ | 623/36 |
| 2003/0074085 A1 * | 4/2003 | Slemker et al. ................ | 623/35 |
| 2004/0059433 A1 * | 3/2004 | Slemker et al. ................ | 623/38 |

FOREIGN PATENT DOCUMENTS

| | | | |
|---|---|---|---|
| GB | 2338899 A | * | 1/2000 |
| JP | 9-164158 | * | 6/1997 |
| WO | WO03041619 | * | 5/2003 |

* cited by examiner

*Primary Examiner*—Alvin J. Stewart
(74) *Attorney, Agent, or Firm*—Ryndak & Suri LLP

(57) ABSTRACT

A locking coupler device for connecting a residual limb socket to a lower limb prosthesis is provided having a body with a top mounting surface, a bottom mounting surface, an anterior area and a posterior area. The top mounting surface is adapted to connect to the residual limb socket at a defined location on the top mounting surface. The bottom mounting surface is adapted to connect to the lower limb prosthesis at a defined location on the bottom mounting surface. The top and bottom mounting surfaces are horizontally offset such that a longitudinal centerline of the residuum limb socket is located from about 0.5 to about 4.0 inches anterior of a longitudinal centerline of the lower limb prosthesis when the residual limb socket and the lower limb prosthesis are attached to the top and bottom mounting surfaces, respectively, of the coupler device. In addition, the top mounting surface is inclined posterior to anterior at an angle from about 5° to about 20° relative to the bottom mounting surface.

36 Claims, 4 Drawing Sheets

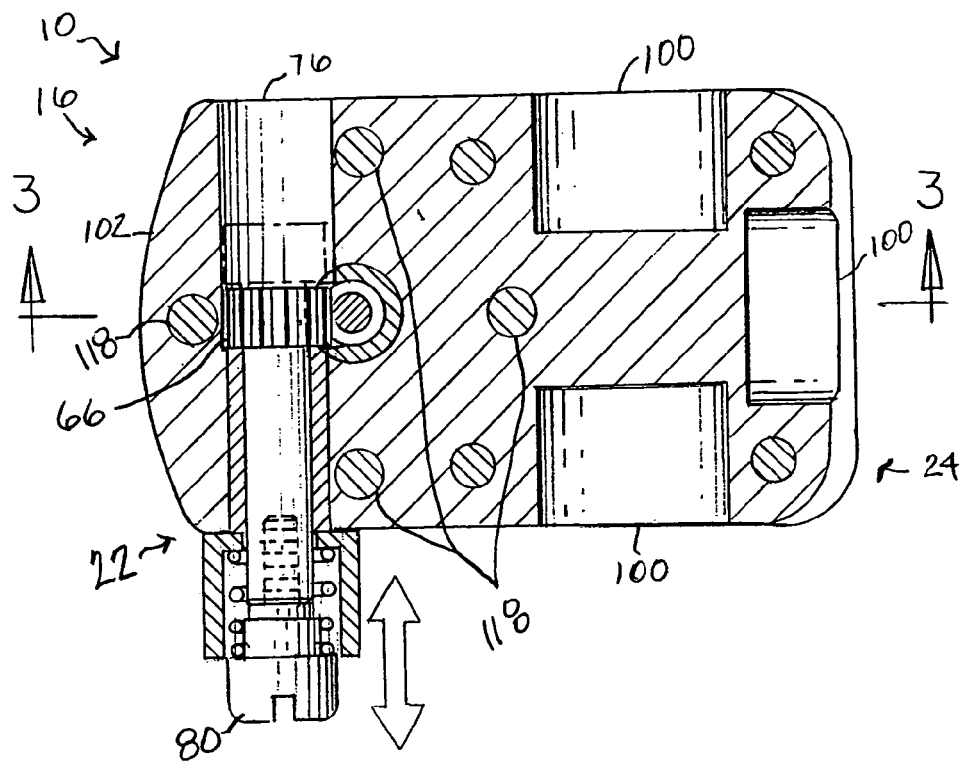
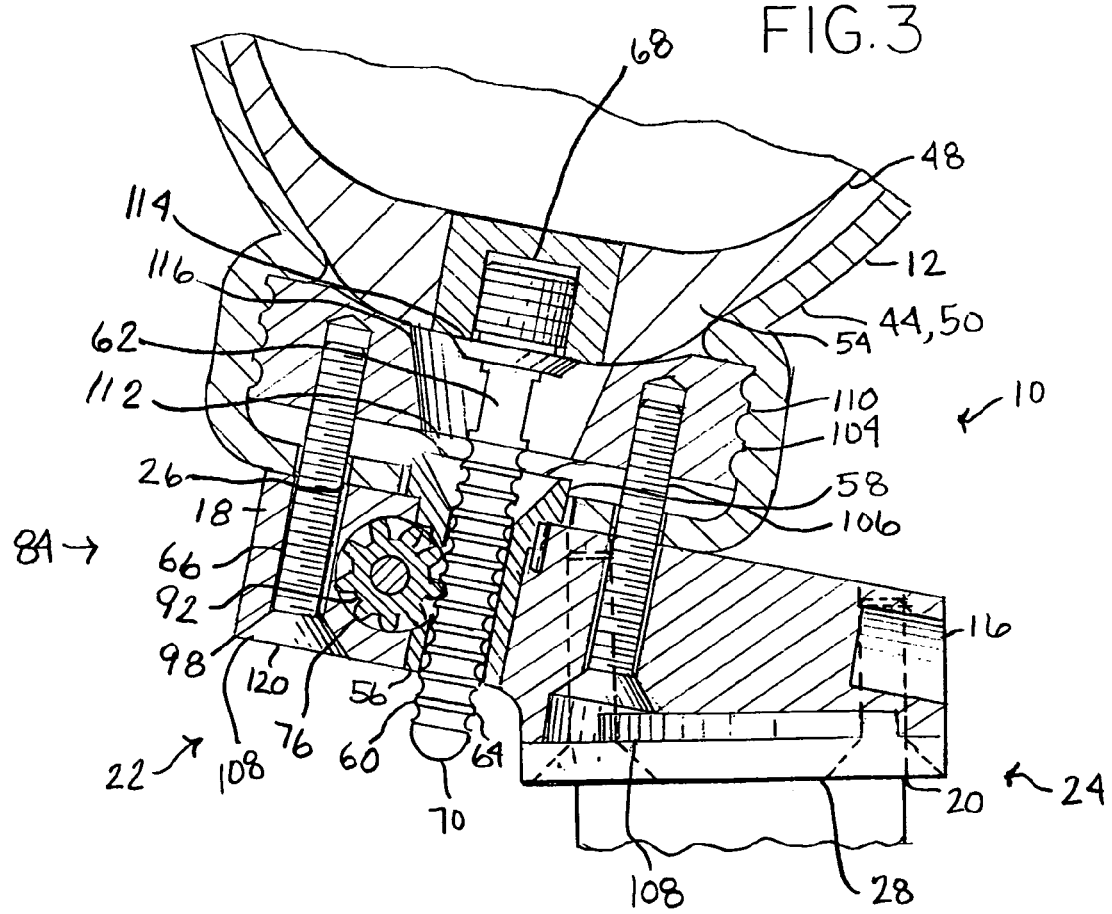

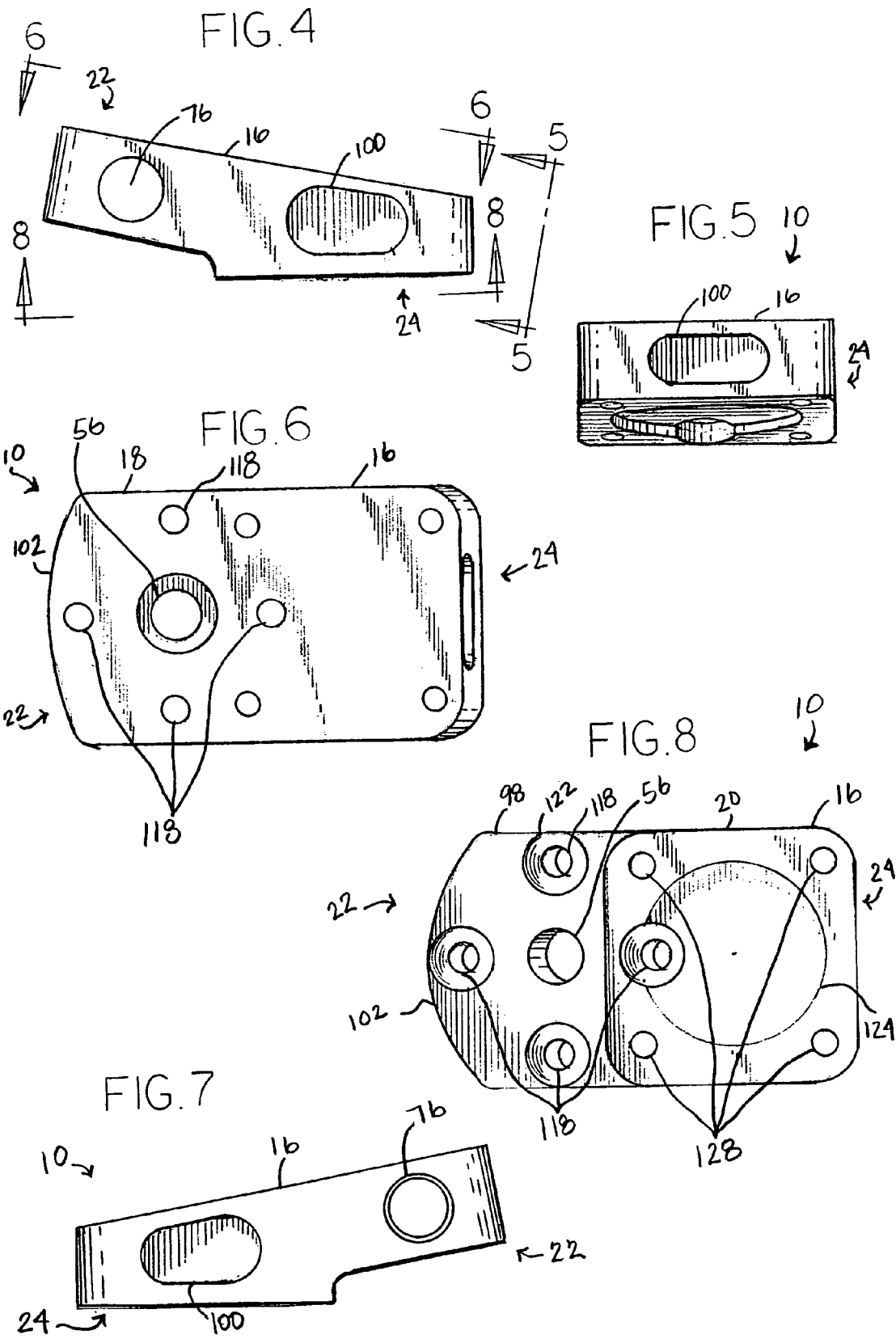

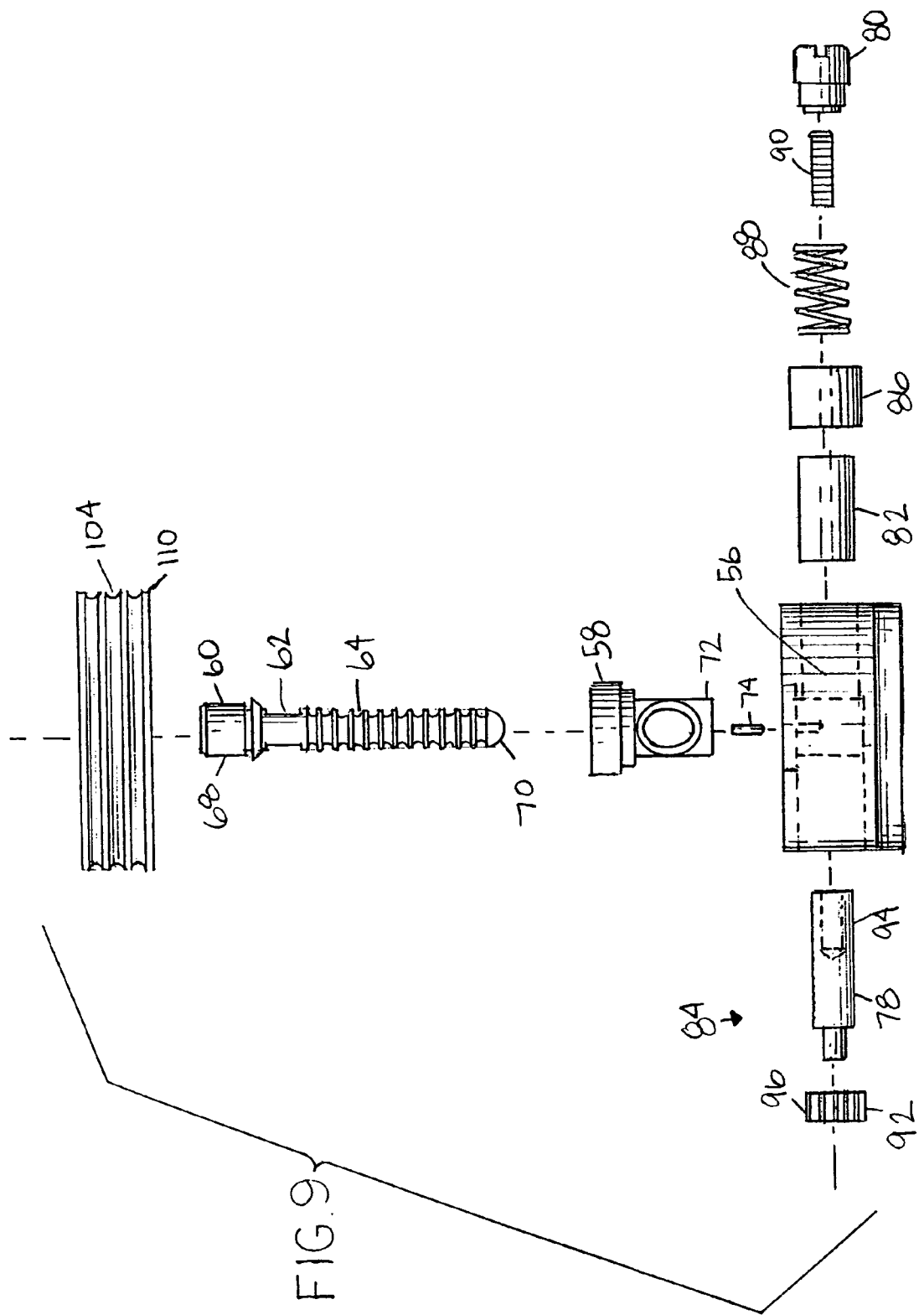

PROSTHETIC ANGLED LOCKING COUPLER DEVICE

TECHNICAL FIELD

This invention relates to a coupler device, and more particularly to a coupler device for connecting a residual limb socket to a lower limb prosthesis.

BACKGROUND OF THE INVENTION

Amputees and other persons with residual limbs often use prosthetic devices, or prostheses. A prosthesis is an artificial device used to replace a missing body part. A transfemoral amputee, a person with a residual limb, or residuum, is missing his lower limb, beginning at his lower thigh (femur) and including the knee through the foot. A prosthesis that simulates the lower limb is often used by a transfemoral amputee. In order to attach the lower limb prosthesis, the residuum is placed into a prosthetic residual limb socket. In order to connect the socket to the lower limb prosthesis, a coupler device is used.

In recent years, use of a plastic or silicone sleeve has gained popularity as a means of suspending the prosthetic socket onto the residuum. A tightly fitting silicone suspension sleeve is rolled onto the residuum. The residuum with the silicone sleeve is then placed into the socket. A pin connects the center of the distal end of a patient's residuum, through a receptacle of the silicone sleeve, to the prosthetic socket and the coupler device via a locking mechanism. When the pin is screwed into the receptacle, it is centered on the end of the residuum. The other end of the pin is inserted into the coupler device that is incorporated into the prosthetic socket. The coupler device also connects the socket to the lower limb prosthesis, which includes a connector, a prosthetic knee joint, a pylon, a tube clamp adapter and a prosthetic foot.

Known locking couplers have the attachment point for the lower limb prosthesis directly in line with the pin and the center of the residuum. This results in co-linearity of the prosthesis with the pin which adversely affects the stability of the prosthesis when there is a flexion contracture of the hip, which occurs often with transfemoral amputees. A need exists for a locking coupler device in which the attachment point for the lower limb prosthesis does not adversely affect the stability of the prosthesis when there is a flexion contraction at the hip, but rather provides for a stable alignment of the prosthesis.

When there is a flexion contracture at the hip, for there to be stable alignment of the prosthesis, the attachment of the prosthetic knee joint and pylon must be along or behind the trochanter-knee-ankle, or TKA, line. A need exists for a coupler device that provides an attachment point of the prosthetic knee joint and pylon along or behind the TKA line.

The requirements that the pin attaches at the center of the distal end of the residuum and that the lower limb prosthesis attaches along or behind the TKA line are mutually exclusive with known locking couplers when a flexion contracture at the hip is present. The pin can be attached at the center of the residuum or the lower limb prosthesis can be attached along the TKA line, but not both. Compromising between these requirements when there is a flexion contracture at the hip results in either 1) inadequate alignment and thus instability if the lower limb prosthesis is not aligned with the TKA line, or 2) inappropriate placement of the attachment pin which restricts donning and doffing the prosthesis if the pin is not attached at the center of the distal end of the residuum.

Because current known locking couplers have the attachment point for the lower limb prosthesis directly in line with the pin and not along the TKA line, the prosthetist is often required to modify the prosthesis to achieve alignment of the knee joint with the TKA line and improve the stability of the prosthesis. To do this, the prosthetist typically creates separate attachment locations on the socket for the pin and for the lower limb prosthesis. The prosthetist attaches a cone of tape or paper to the socket at the location where the lower limb prosthesis is to be attached. The cone is then packed with a filler material which bonds to the socket. When the filler material has dried, the cone can be removed. However, filler material also bonds to the cone and as a result, the cone often cannot be completely removed. Further, the filler material is very heavy. The resulting prosthesis is heavy, bulky and aesthetically unappealing.

A need exists for a locking coupler device that does not require a prosthetist to modify the prosthesis by creating separate attachment locations on the socket for the pin and the attachment point for the rest of the prosthesis. A need also exists for a prefabricated locking coupler device that allows the lower limb prosthesis to attach to the coupler device along or behind the TKA line while allowing the attachment point on the top surface of the locking coupler device to align with the center of the distal end of the residuum.

The sleeve covered residuum is typically drawn into the socket using a tool. A need exists for a coupling device that allows the pin and thus the residuum to be drawn into the socket without a separate tool. A need also exists for a coupler device that is lightweight and aesthetically appealing.

SUMMARY OF THE INVENTION

In accordance with the present invention, a locking coupler device for connecting a residuum limb socket to a lower limb prosthesis is provided. In one embodiment, the locking coupler device comprises a coupler body, an attachment ring, a pin, an alignment bushing, and a locking mechanism. Typically, the coupler body is composed of a lightweight material, preferably aluminum. The body has a top mounting surface and a bottom mounting surface, an anterior area and a posterior area. The top mounting surface of the body is adapted to connect to the residuum limb socket at a defined location on the top mounting surface. The bottom mounting surface of the body is adapted to connect to the lower limb prosthesis at a defined location on the bottom mounting surface. The coupler device allows for attachment of the lower limb prosthesis along or behind the trochanter-knee-ankle, or TKA, line.

In accordance with one aspect of the invention, the top and bottom mounting surfaces are horizontally offset such that a longitudinal centerline of the residual limb socket is located from about 0.5 to about 4.0 inches anterior of a longitudinal centerline of the lower limb prosthesis when the residual limb socket and the lower limb prosthesis are attached to the top and bottom mounting surfaces, respectively. The horizontal offset permits some compensation for the position of the center of the residuum relative to the TKA line. In another embodiment, the longitudinal centerline of the residual limb socket is located from about 0.5 to about 3.0 inches anterior of the longitudinal centerline of the lower limb prosthesis when the residual limb socket and the lower limb prosthesis are attached to the top and bottom mounting surfaces, respectively. In yet another embodiment, the longitudinal centerline of the residual limb socket is located from about 1.0 to about 2.0 inches anterior of the longitudinal centerline of the lower limb prosthesis when the residual limb socket and the lower limb prosthesis are attached to the top and bottom mounting surfaces, respectively. In the preferred embodiment, the longitudinal centerline of the residual limb socket is located about 1.25 inches anterior of the longitudinal centerline of the lower limb prosthesis when the residual limb socket and the lower limb prosthesis are attached to the top and bottom mounting surfaces, respectively.

In accordance with another aspect of the invention, the top mounting surface is inclined posterior to anterior at an angle from about 5° to about 30° relative to the bottom mounting surface. This angle further compensates for the position of the center of the residuum relative to the TKA line. In another embodiment, the top mounting surface is inclined posterior to anterior at an angle from about 8° to about 15° relative to the bottom mounting surface. In the preferred embodiment, the top mounting surface is inclined posterior to anterior at an angle of about 10° relative to the bottom mounting surface.

In accordance with yet another aspect of the invention, in one embodiment the coupler body includes at least one recess to reduce the weight of the body. Preferably, the recesses are elliptical. However, a practitioner skilled in the art will understand that the recesses can be of any suitable size and shape to reduce the weight of the coupler without affecting the structural integrity of the body. The coupler body also includes a face on its anterior area. In the preferred embodiment, the face is rounded.

In accordance with another aspect of the invention, in one embodiment the top mounting surface of the body includes a set of apertures for receiving a set of attachment screws to attach the coupler to the socket. In the preferred embodiment, the first set of apertures consists of four apertures configured in a standard four-hole spacing arrangement used by current modular prostheses and each of the apertures in the set tapers outward at the bottom surface of the body. When the attachment screws are secured to the attachment ring, the heads of the attachment screws will align with the outward tapering areas and the screws will be flush with the bottom surface.

In accordance with another aspect of the invention, in one embodiment the body has a large aperture that aligns with the center of the distal end of the residuum. The large aperture is sized to receive an alignment bushing.

In accordance with yet another aspect of the invention, in one embodiment the bottom mounting surface of the body includes a circular recess that is adapted for a connector or a prosthetic knee joint. Surrounding the circular recess is a set of apertures in the body. Preferably, the set of apertures is composed of four apertures configured in the standard four-hole spacing arrangement to allow for the use of a variety of standard connectors or knee joints. In the preferred embodiment, the second set of apertures is threaded.

In accordance with another aspect of the invention, the body of the coupler attaches to the socket with the attachment ring. The attachment ring is placed in the base of the socket. The attachment ring becomes embedded in and integral with the socket. Preferably, the attachment ring has a set of threaded apertures for receiving attachment screws. The apertures correspond and align with the set of apertures on the top mounting surface of the coupler body. The socket has a corresponding set of apertures. The attachment screws pass through the apparatus in the socket and mate with the threaded apparatus in the attachment ring. In the preferred embodiment, the set of apertures in the attachment ring are configured in a standard four-hole spacing arrangement.

In accordance with another aspect of the invention, the attachment ring has three spherical grooves to assist in embedding it into the socket and to ensure that it does not loosen from the socket. The attachment ring has a keyway which is used to both indicate the anterior position of the body required for proper positioning of the prosthesis and to prevent rotation of the attachment ring within the socket. The attachment ring has a large aperture for receiving the pin. The large aperture of the attachment ring has a spherical tapering recess. Preferably, the tapering recess is smooth and lacks the boss found on other rings.

In accordance with yet another aspect of the invention, attachment screws are used to hold the coupler body to the socket. The attachment screws pass through the set of apertures on the top mounting surface of the coupler body, the set of apertures in the socket, and mate with the threaded apertures in the attachment ring. When the attachment screws are fully tightened, their heads are engaged in the tapered recesses of the first set of apertures in the body.

In accordance with another aspect of the invention, the coupler has a pin. The pin is screwed into a receptacle in the silicone sleeve and attaches the silicon sleeve to the socket, and then the socket to the coupler body. The pin in its engaged position in the receptacle in the sleeve is centered on the end of the residuum. The pin passes through the large aperture in the attachment ring and into an alignment bushing. The pin has a series of elevated rings along its shaft. These rings allow the pin to be locked into place by the locking mechanism. The pin is removably attached to the coupler. The coupler is designed to mate with pins of standard prosthetic devices. Thus, although it is preferred, it is not necessary that an improved pin be used with the coupler.

In the preferred embodiment, the pin has an overall length of about 2½ inches, with a locking length of about 2 inches. The proximal end of the pin is threaded to mate with the threaded receptacle in the silicon sleeve. In the preferred embodiment, the distal end of the pin is semi-spherical without any lips or ridges. This prevents the pin from catching or getting hung up when the pin is being inserted or the prosthesis is being donned. In the preferred embodiment, the distal end of the pin has a transverse aperture. The patient, caregiver or prosthetist can insert a string, wire, cable or other suitable material through the transverse aperture. Once the material is secured to the pin, the material can be fed through the alignment bushing and guide the pin into the alignment bushing. After the pin is locked in place, the wire can be removed.

In accordance with another aspect of the invention, the coupler body includes a transverse aperture for holding the locking mechanism. The locking mechanism consists of a toothed plunger, a button thumbscrew, a button housing, a clutch, a setscrew, a spring and a needle bearing. The locking mechanism is housed in the transverse aperture in the coupler body. Because the transverse aperture intersects the large aperture when the pin is inserted into the alignment bushing, it associates with the toothed plunger or the locking mechanism.

In accordance with another aspect of the invention, the toothed plunger consists of a pinion and a shaft. The pinion mates with the elevated rings on the shaft of the pin. As the pinion rotates, the pin is drawn into the coupler or exits the coupler. Preferably, the teeth on the pinion are spaced apart such that the pinion can accept pins from a variety of liners and sleeves. In an alternate embodiment, a pinion with a one-way ratchet may be used.

In the preferred embodiment, the length of the shaft is about 1.39 inches. This reduces the amount of locking mechanism that protrudes from the body of the coupler at the button thumbscrew.

In the preferred embodiment, the button thumbscrew has a diameter of less than 0.465 inches and the overall length of the button thumbscrew is about 0.74 inches. The button thumbscrew is slotted to facilitate turning the pinion to draw the limb into the socket with a tool. In one embodiment, the button thumbscrew is knurled to facilitate turning the pinion to draw the limb into the socket without a tool, but rather with a person's hand grip. The button housing fits the button thumbscrew and the spring. The button housing may be replaced with rubber stock or elastomeric bellows.

In accordance with another aspect of the invention, the button thumbscrew is part of a unidirectional locking mechanism. Because the locking mechanism has a clutch, when the button thumbscrew is in its engaged position, the pin can be drawn into the alignment bushing. The pin cannot be removed from the coupler unless the button thumbscrew is depressed, thus disengaging the locking mechanism. When the button thumbscrew is depressed, the pin can be removed from the coupler.

In accordance with another aspect of the invention, the large aperture in the body that aligns with the center of the residuum is adapted to accept an alignment bushing. The preferred alignment bushing is made from hardened tool steel. However, other materials known in the art to be suitable for this purpose may be used, such as plastic, for example. The alignment bushing is designed to prohibit any rotation of it relative to the locking mechanism that could prevent the locking mechanism from disengaging.

In accordance with another aspect of the invention, the pin is threaded through the alignment bushing. As the pin is drawn through the alignment bushing using a tool or the thumbscrew on the button thumbscrew, it pulls the liner and, thus, the residuum covered with the liner, into the socket.

In accordance with another aspect of the invention, a connector is typically used to connect the coupler device to the prosthetic knee joint. The connector allows for between 0° and 8° of angular offset from the top mounting surface of the body. If the bottom mounting surface of the body of the coupler is inclined 10° to the top mounting surface, the lower limb prosthesis can have an angular offset of between 10° and 18° using a connector. Attachment screws attach the connector to the coupler device. The connector is attached to the prosthetic knee joint. If the patient is tall, the coupler device may be attached directly to the prosthetic knee joint. Attached to the prosthetic knee joint is the shin pylon. Beneath the shin pylon is a tube clamp adapter that connects the shin pylon to the prosthetic foot. The prosthetic foot can be made of metal, plastic or any suitable material. It is not necessary that the prosthetic foot resemble an anatomical foot.

Numerous advantages may be provided with the coupler device of the present invention. An above the knee amputee or other person with a residual limb will use a prosthetic leg with a prosthetic knee joint and foot to simulate the missing limb and to allow for standing and/or walking. Known locking coupler devices have the attachment point for the lower limb prosthesis directly in line with the pin and the center of the residuum. This results in co-linearity of the prosthesis with the pin which adversely affects the stability of the prosthesis when there is a flexion contracture of the hip. When there is a flexion contracture at the hip, which often occurs with transfemoral amputees, for there to be a stable alignment of the prosthesis, the attachment of the prosthetic knee joint must be along or behind the trochanter-knee-ankle, or TKA, line.

The locking coupler device permits connection of the residuum to the lower limb prosthesis and allows for attachment of the lower limb prosthesis along or behind the TKA line, which provides the highest degree of stability for the person. It also allows the prosthetist to use a prefabricated part to properly align the lower limb prosthesis for stability rather than having to individually craft an attachment by modifying the known prosthesis to achieve alignment of the knee joint. It also allows for a lightweight coupler.

One aspect of the invention includes using a standard four-hole spacing configuration on the set of apertures on the top mounting surface of the body for receiving a set of attachment screws to attach the coupler device to the socket. This is advantageous because if the patient's flexion contracture improves or the need for an angled offset is eliminated, the coupler device of the present invention can be replaced with a standard coupler device. Similarly, if a flexion contracture develops, the coupler device of the present invention can be substituted into a patient's existing prosthesis.

A standard four-hole spacing in the attachment ring also allows for the exchange of coupler devices if the patient's flexion contracture improves and an angled offset is no longer warranted. Conversely, a coupler device of the present invention may be added to an existing prosthesis to accommodate a flexion contracture that was overlooked or recently developed. When the coupler is used with an existing prosthesis, the attachment ring already associated with the patient's socket is used.

In one embodiment, the anterior area of the coupler body of the present invention includes a face that is tapered. Tapering the face will reduce the weight of the coupler and reduce catching or snagging of the coupler on the patient's clothing.

The smooth tapering recess of the large aperture of the attachment ring allows for an accurate insertion of the pin into the coupler.

In one embodiment, the small diameter button thumbscrew of the locking mechanism allows for a smaller button housing which reduces the bulkiness of the coupler and reduces the amount of protrusion on the side of the coupler at the button thumbscrew and reduces its likelihood of catching on the patient's clothing. The small length of the button thumbscrew reduces the amount of protrusion on the side of the coupler at the button thumbscrew.

In one embodiment, the hardened tool steel material makes up the alignment bushing to reduce or eliminate wear sometimes experienced with plastic bushings. This embodiment also has the benefit of reducing or eliminating wear on the body of the coupler.

BRIEF DESCRIPTION OF THE DRAWINGS

FIG. 2 illustrates a sectional perspective view of the device taken along line 2—2 of FIG. 1;

FIG. 3 illustrates a sectional perspective view of the device taken along line 3—3 of FIG. 2;

FIG. 4 illustrates a right side elevation view of the device of FIG. 1;

FIG. 5 illustrates a sectional perspective view of the device taken along line 5—5 of FIG. 4;

FIG. 6 illustrates a sectional perspective view of the device taken along line 6—6 of FIG. 4;

FIG. 7 illustrates a left side elevation view of the device of FIG. 1;

FIG. 8 illustrates a sectional perspective view of the device taken along line 8—8 of FIG. 4;

FIG. 9 illustrates a disassembled view of the locking mechanism of the device of FIG. 1.

DETAILED DESCRIPTION OF THE INVENTION

Figure 1:
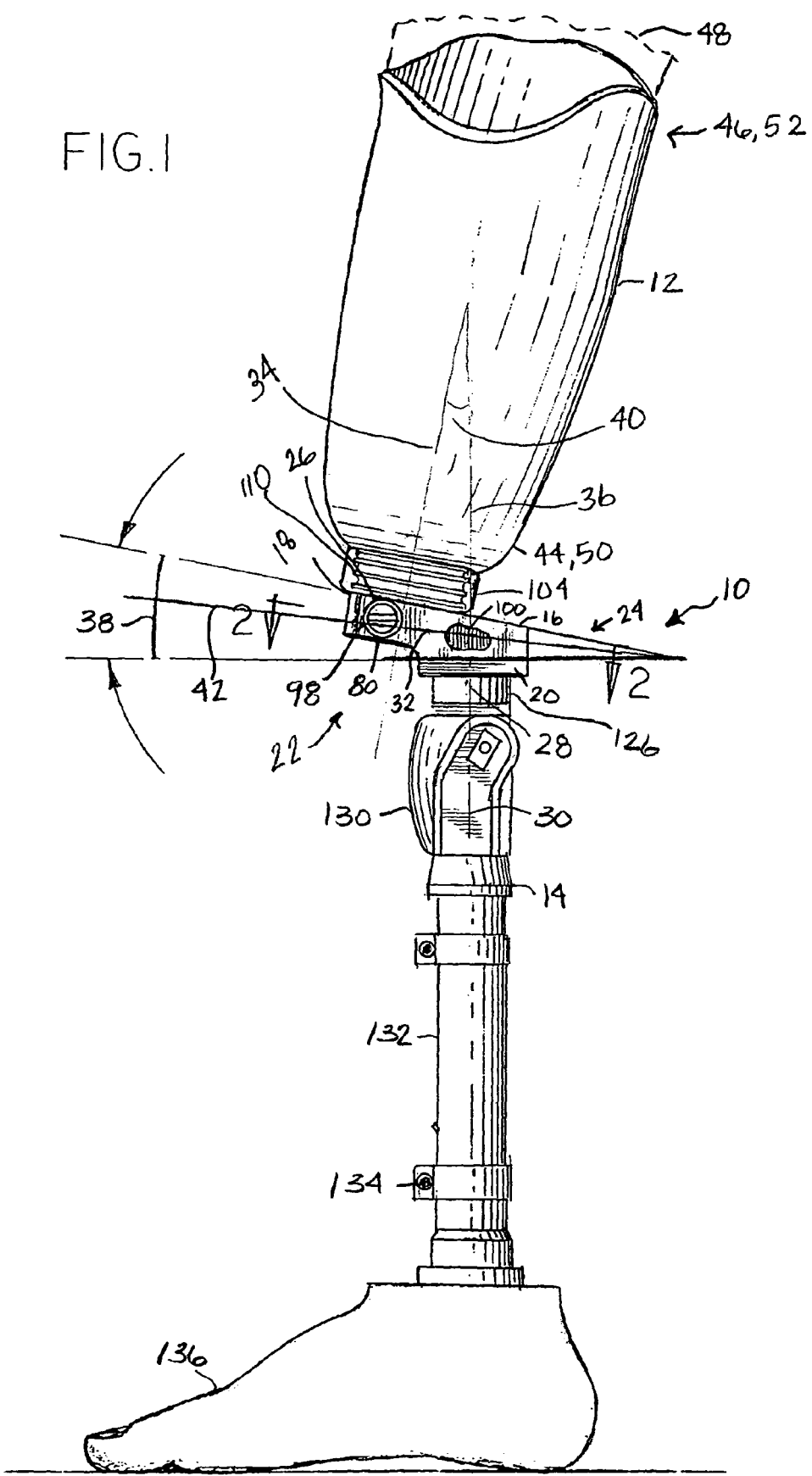
FIG. 1 illustrates a medial view of a whole prosthesis incorporating a device in accordance with the present invention.

Referring to the figures generally, there is illustrated a coupler device 10 for connecting a residual limb socket 12 to a lower limb prosthesis 14 in accordance with the invention. Coupler device 10 includes a coupler body 16 that includes a top mounting surface 18 and a bottom mounting surface 20, as best illustrated in FIGS. 6 and 8, respectively, and an anterior area 22 and a posterior area 24, as illustrated in the figures generally. Body 16 is composed of a lightweight material, preferably aluminum. Top mounting surface 18 is adapted to connect to residual limb socket 12 at a defined location 26 of top mounting surface 18, as illustrated in FIGS. 1 and 3. Bottom mounting surface 20 is adapted to connect to lower limb prosthesis 14 at a defined location 28 of bottom mounting surface 20, as illustrated in FIG. 1. Coupler device 10 allows for attachment of lower limb prosthesis 14 along or behind the trochanter-knee-ankle, or TKA, line 30, as best illustrated in FIG. 1.

Top mounting surface 18 and bottom mounting surface 20 are horizontally offset 32 such that a longitudinal centerline 34 of residual limb socket 12 is located from about 0.5 to about 4.0 inches anterior 22 of a longitudinal centerline 36 of lower limb prosthesis 14 when residual limb socket 12 and lower limb prosthesis 14 are attached to top mounting surface 18 and bottom mounting surface 20, respectively, of coupler device 10, as illustrated in FIG. 1. The horizontal offset 32 of longitudinal centerlines 34 and 36 of residual limb socket 12 and lower limb prosthesis 14, respectively, permits some compensation for the position of defined location 26 of top mounting surface 18 relative to TKA line 30. Alternatively, longitudinal centerline 34 of residual limb socket 12 is located from about 0.5 inches to about 3.0 inches anterior 22 of longitudinal centerline 36 of lower limb prosthesis 14 when residual limb socket 12 and lower limb prosthesis 14 are attached to top mounting surface 18 and bottom mounting surface 20, respectively, of coupler device 10. Alternatively, longitudinal centerline 34 of residual limb socket 12 is located from about 1.0 to about 2.0 inches anterior 22 of longitudinal centerline 36 of lower limb prosthesis 14 when residual limb socket 12 and lower limb prosthesis 14 are attached to top mounting surface 18 and bottom mounting surface 20, respectively, of coupler device 10. Preferably, longitudinal centerline 34 of residual limb socket 12 is located about 1.25 inches anterior 22 of longitudinal centerline 36 of lower limb prosthesis 14 when residual limb socket 12 and lower limb prosthesis 14 are attached to top mounting surface 18 and bottom mounting surface 20, respectively, of coupler device 10.

Top mounting surface 18 is inclined posterior 24 to anterior 22 at an angle 38 from about 5° to about 20° relative to bottom mounting surface 20, as illustrated in FIG. 1. Angle 38 further compensates for the position of defined location 26 of top mounting surface 18 relative to TKA line 30. Alternatively, top mounting surface 18 is inclined posterior 24 to anterior 22 at angle 38 from about 8° to about 15° relative to bottom mounting surface 20. Preferably, top mounting surface 18 is inclined posterior 24 to anterior 22 at angle 38 of about 10° relative to bottom mounting surface 20. Angle 38 is equal to an angle 40 that is the angle that results from the intersection of longitudinal centerlines 34 and 36 of residual limb socket 12 and lower limb prosthesis 14, respectively.

Horizontal offset 32 is ascertained by measuring the distance between longitudinal centerlines 34 and 36 of residual limb socket 12 and lower limb prosthesis 14, respectively, along a midpoint line 42 of angle 38.

Residual limb socket 12 is custom made to fit a person's residuum. Residual limb socket 12 further includes a distal end 44 and a proximal end 46 and contains a sleeve 48 that has a distal end 50 and a proximal end 52, as illustrated in FIGS. 1 and 3. Sleeve 48 may be a liner. Sleeve 48 is preferably composed of silicone, or similar material. Distal end 50 of sleeve 48 houses a receptacle 54, as best illustrated in FIG. 3.

Coupler body 16 further includes an aperture 56 of top mounting surface 18 that is sized to receive both an alignment bushing 58 and pin 60, as illustrated in FIGS. 3, 6, 8 and 9. Pin 60 is screwed into receptacle 54 in sleeve 48 and attaches sleeve 48 to coupler body 16, as best illustrated in FIG. 3. Pin 60 in its engaged position in receptacle 54 in sleeve 48 is centered on distal end 44 of residual limb socket 12, as best illustrated in FIG. 3. Pin 60 passes through aperture 56 of top mounting surface 18 and into alignment bushing 58, as illustrated in FIGS. 3 and 9.

Pin 60 has a shaft 62 which has a series of elevated rings 64, as illustrated in FIGS. 3 and 9. Elevated rings 64 allow pin 60 to be locked into place by locking mechanism 66. Pin 60 is removably attached to coupler device 10. Pin 60 is a standard pin used in standard prosthetic devices. Pin 60 has a proximal end 68 and a distal end 70. Pin 60 has an overall length of about 2.5 inches, with a locking length of about 2 inches. Proximal end 68 of pin 60 is threaded to mate with threaded receptacle 54 in sleeve 48, as illustrated in FIG. 3. Preferably, distal end 50 of sleeve 48 is semi-spherical without any lips or ridges. This prevents pin 60 from catching or getting hung up when pin 60 is being inserted or the prosthesis is being donned. Preferably, distal end 70 of pin 60 includes a transverse aperture.

Alignment bushing 58 is preferably composed of hardened tool steel. However, other materials known in the art to be suitable for this purpose may be used, such as, for example, plastic. Hardened tool steel will eliminate wear sometimes experienced with plastic bushings. It will also eliminate some of the wear on coupler device 10. Alignment bushing 58 is designed to prohibit any rotation of itself relative to locking mechanism 66 that could prevent locking mechanism 66 from disengaging. Alignment bushing 58 has a notch 72 that is adapted to fit a dowel pin 74, as illustrated in FIG. 9. Pin 60 is threaded through alignment bushing 58, as illustrated in FIG. 3. As pin 60 is drawn through alignment bushing 58, it pulls sleeve 48 and thus, residuum covered with sleeve 48 into residual limb socket 12.

Coupler body 16 further includes a transverse aperture 76, as illustrated in FIGS. 2, 4 and 7. Transverse aperture 76 intersects aperture 56 of top mounting surface 18. Transverse aperture 76 houses locking mechanism 66, as illustrated in FIG. 2. Locking mechanism 66 includes a toothed plunger 78, a button thumbscrew 80, a clutch and needle bearing assembly 82, a button housing 86, a spring 88 and a set screw 90, as illustrated in FIG. 9. Because transverse aperture 76 intersects aperture 56 when pin 60 is inserted into alignment bushing 58, it associates with toothed plunger 78 or locking mechanism 66.

Toothed plunger 78 includes a pinion 92 and a shaft 94, as illustrated in FIG. 9. Pinion 92 has teeth 96 that are spaced apart. Pinion 92 mates with elevated rings 64 on shaft 62 of pin 60, as illustrated in FIG. 3. As pinion 92 rotates, pin 60 is drawn into coupler body 16 or exits coupler body 16. Pinion 92 can have a clutch or shuttle lock 84 or a one-way ratchet (not shown). Shaft 94 has a length preferably about 1.39 inches, which reduces the amount of locking mechanism 66 that protrudes from coupler body 16 at bottom 98 of coupler body 16.

Button thumbscrew 80 has a diameter of less than 0.465 inches. This allows for a smaller button housing 86 which reduces the bulkiness of coupler device 10 and reduces its likelihood of catching on the patient's clothing. Preferably, the overall length of button thumbscrew 80 is about 0.74 inches. Button housing 86 fits button thumbscrew 80 and spring 88, as illustrated in FIG. 9. Button housing 86 may be replaced with stock rubber or elastomeric bellows.

Button thumbscrew 80 is part of a unidirectional locking mechanism. Locking mechanism 66 has a shuttle or clutch lock 84 so that when button thumbscrew 80 is in its engaged position, pin 60 can be drawn into alignment bushing 58. Pin 60 cannot be removed from coupler device 10 unless button thumbscrew 80 is depressed, thus disengaging locking mechanism 66. Button thumbscrew 80 may include a thumbscrew. Alternatively, locking mechanism 66 may include a one-way ratchet mechanism (not shown).

Coupler body 16 further includes at least one recess 100, as illustrated in FIGS. 1, 4, 5 and 7. Recess 100 reduces the weight of coupler body 16 while minimizing loss of strength. Recess 100 is preferably elliptical. However, a practitioner skilled in the art will understand that recess 100 can be of any suitable size and shape to reduce the weight of coupler body 16 without affecting the structural integrity of body 16.

Anterior area 22 of coupler body 16 includes a face 102 that is rounded, as illustrated in FIGS. 2, 6 and 8. Rounded face 102 reduces the weight of coupler body 16 and reduces catching or snagging of coupler device 10 on the patient's clothing.

Residual limb socket 12 further includes an attachment ring 104, as illustrated in FIGS. 1, 3 and 9. Coupler body 16 attaches to residual limb socket 12 with attachment ring 104. Attachment ring 104 is placed in the distal end 44 of residual limb socket 12, as illustrated in FIGS. 1 and 3. Attachment ring 104 becomes embedded in and integral with residual limb socket 12. Attachment ring 104 further includes a set of four apertures 106 configured in a standard four-hole spacing arrangement. Apertures 106 are threaded and adapted to receive attachment screws 108, as illustrated in FIG. 3.

Attachment ring 104 further includes three spherical grooves 110 to assist in embedding it in residual limb socket 12 and to ensure that it does not loosen from socket 12, as illustrated in FIGS. 1, 3 and 9. Attachment ring 104 further includes a keyway 112, as illustrated in FIG. 3. Keyway 112 is used to both indicate anterior 22 position of coupler body 16 required for proper positioning and prevent rotation of attachment ring 104 within socket 12. Pin 60 passes through keyway 112 to attach sleeve 48 to body 16, as illustrated in FIG. 3. Attachment ring 104 further includes a large aperture 114 for receiving pin 60, as illustrated in FIG. 3. Large aperture 114 includes a cylindrical recess 116. Preferably, cylindrical recess 116 is smooth.

Top mounting surface 18 further includes a set of four apertures 118 configured in a standard four-hole spacing arrangement, as illustrated in FIGS. 2, 6 and 8. Apertures 118 receive attachment screws 108 that include heads 120 that attach coupler body 16 to residual limb socket 12 through attachment ring 104. Preferably, apertures 118 each include outward tapering areas 122 at bottom 98 of coupler device 10, as best illustrated in FIG. 8. When attachment screws 108 are secured into attachment ring 104, heads 120 align with outward tapering areas 122 and attachment screws 108 will be flush with bottom surface 98, as illustrated in FIG. 2. This will eliminate snagging of the patients' clothing.

Bottom mounting surface 20 further includes a circular recess 124 that is adapted for a connector 126 that will further secure bottom mounting surface 20 to lower limb prosthesis 14, as illustrated in FIGS. 5 and 8. Surrounding circular recess 124 is a set of four apertures 128 configured in a standard four-hole spacing arrangement, as illustrated in FIG. 8. Apertures 128 are preferably threaded. Apertures 128 receive attachment screws 108 that attach coupler body 16 to connector 126. Connector 126 is attached to a prosthetic knee joint 130, which connects to a shin pylon 132, which connects to a tube clamp adapter 134, which connects to a prosthetic foot 136, as illustrated in FIG. 1. If the patient is tall, bottom mounting surface 20 may be attached directly to prosthetic knee joint 130. Prosthetic foot 136 can be made of metal, plastic, or any suitable material. It is not necessary that prosthetic foot 136 resemble an anatomical foot.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. A coupler device for connecting a residual limb socket to a lower limb prosthesis comprising:
    a coupler body having a top mounting surface and a bottom mounting surface and having an anterior area and a posterior area;
    said top mounting surface connecting said top mounting surface to a residual limb socket at a defined location on said top mounting surface;
    said bottom mounting surface being adapted to connect said bottom mounting surface to said lower limb prosthesis at a defined location on said bottom mounting surface;
    said top and bottom mounting surfaces being horizontally offset such that a longitudinal centerline of said residual limb socket is located from about 0.5 to about 4.0 inches anterior of a longitudinal centerline of the lower limb prosthesis when said residual limb socket and said lower limb prosthesis are attached to the top and bottom mounting surfaces, respectively, of the coupler device;
    said top mounting surface being inclined in the posterior to anterior direction at an angle from about 5° to about 20° relative to said bottom mounting surface;
    said residual limb socket having a distal end and a proximal end, and said residual limb socket being attached to a sleeve having a proximal end and a distal end housing a receptacle;
    wherein said coupler body further comprises an aperture on said top mounting surface receiving both an alignment bushing and a pin, said pin comprising a shaft and a series of elevated rings along said shaft and said alignment bushing includes a notch that is sized to fit a dowel pin, and a transverse aperture at the top mounting surface which intersects said aperture of said top mounting surface when said pin is inserted.

2. The device of claim 1 wherein said longitudinal centerline of said residual limb socket is located from about 0.5 inches to about 3 inches anterior of said longitudinal centerline of said lower limb prosthesis when the residual limb socket and the lower limb prosthesis are attached to the top and bottom mounting surfaces, respectively.

3. The device of claim 1 wherein said longitudinal centerline of said residual limb socket is located from about 1 inch to about 2 inches anterior of said longitudinal centerline of said lower limb prosthesis when the residual limb socket and the lower limb prosthesis are attached to the top and bottom mounting surfaces, respectively.

4. The device of claim 1 wherein said longitudinal centerline of said residual limb socket is located about 1.25 inches anterior of said longitudinal centerline of said lower limb prosthesis when the residual limb socket and the lower limb prosthesis are attached to the top and bottom mounting surfaces, respectively.

5. The device of claim 1 wherein said top mounting surface is inclined posterior to anterior at an angle from about 8° to about 15° relative to said bottom mounting surface.

6. The device of claim 1 wherein said top mounting surface is inclined posterior to anterior at an angle of about 10° relative to said bottom mounting surface.

7. The device of claim 1 wherein said longitudinal centerline of said lower limb prosthesis is aligned along or behind a patient TKA (trochanter-knee-ankle) line.

8. The device of claim 1 wherein said receptacle is threaded.

9. The device of claim 1 wherein said pin is threaded.

10. The device of claim 1 wherein said pin is shaped, dimensioned and oriented to be inserted into said receptacle, so as to pass through said aperture into said alignment bushing and pull said sleeve enclosed residuum into said residual limb socket and further attach said sleeve to said coupler body.

11. The device of claim 10 wherein said pin is centered on said distal end of said socket when said pin is engaged in said receptacle.

12. The device of claim 10 wherein said distal end of said socket further includes an attachment ring that has an inner side and a keyway and said pin passes through said keyway to attach said sleeve to said body.

13. The device of claim 12 wherein said attachment ring further comprises a set of four apertures surrounding said keyway in a standard four-hole spacing arrangement.

14. The device of claim 13 wherein said attachment ring includes three spherical grooves and has a cylindrical recess on said inner side.

15. The device of claim 13 wherein said top mounting surface further comprises a set of four apertures surrounding said aperture in a standard four-hole spacing arrangement.

16. The device of claim 15 wherein said apertures of said set of apertures of said top mounting surface receive attachment screws that attach said coupler body to said socket through said set of apertures of said attachment ring.

17. The device of claim 1 wherein said pin has a length of not more than about 2.5 inches and a locking length of about 2 inches.

18. The device of claim 1 wherein said pin has a distal tip that is semi-spherical.

19. The device of claim 18 wherein said distal tip further includes a transverse aperture.

20. The device of claim 1 wherein said body further comprises at least one recess.

21. The device of claim 20 wherein said recess is elliptical.

22. The device of claim 1 wherein said anterior area of said coupler body includes a face that is rounded.

23. The device of claim 1 wherein said bottom mounting surface further comprises a set of four apertures configured in a standard four-hole spacing arrangement.

24. The device of claim 23 wherein said apertures include lower surfaces that are threaded.

25. The device of claim 24 wherein said apertures of said set of apertures of said bottom mounting surface receive attachment screws that attach said coupler body to a connector or to a prosthetic knee joint.

26. The device of claim 1 wherein said bottom mounting surface connects to a prosthetic knee joint, which connects to a shin pylon, which connects to a tube clamp adapter, which connects to a prosthetic foot.

27. A coupler for connecting a residual limb socket to a lower limb prosthesis comprising:
a coupler body having a top mounting surface and a bottom mounting surface and having an anterior area and a posterior area;
said top mounting surface connecting said top mounting surface to a residual limb socket at a defined location on said top mounting surface;
said bottom mounting surface connecting said bottom mounting surface to said lower limb prosthesis at a defined location on said bottom mounting surface;
said top and bottom mounting surfaces being horizontally offset such that a longitudinal centerline of said residual limb socket is located from about 0.5 to about 4.0 inches anterior of a longitudinal centerline of the lower limb prosthesis when said residual limb socket and said lower limb prosthesis are attached to the top and bottom mounting surfaces. respectively, of the coupler device;
said top mounting surface being inclined in the posterior to anterior direction at an angle from about 5° to about 20° relative to said bottom mounting surface;
said residual limb socket having a distal end and a proximal end, and said residual limb socket being attached to a sleeve having a proximal end and a distal end housing a receptacle;
wherein said coupler body further comprises an aperture on said top
mounting surface receiving both an alignment bushing and a pin, said pin comprising a shaft and a series of elevated rings along said shaft, and a transverse aperture at the top mounting surface which intersects said aperture of said top mounting surface when said pin is inserted, and said transverse aperture houses a locking mechanism.

28. The device of claim 27 wherein said locking mechanism further comprises a toothed plunger, a button thumbscrew, a button clutch, a needle bearing, a button housing, a spring and a set screw.

29. The device of claim 28 wherein said button thumbscrew has a thumbscrew.

30. The device of claim 28 wherein said toothed plunger comprises a pinion and a shaft.

31. The device of claim 30 wherein said pinion includes teeth that are spaced apart.

32. The device of claim 31 wherein as said pinion rotates, said pinion mates with said elevated rings of said pin and said pin is drawn into said body or exits said body.

33. The device of claim 30 wherein said pinion comprises a clutch bearing.

34. The device of claim 30 wherein said pinion comprises a one-way ratchet.

35. A method of attaching a residual limb socket to a lower limb prosthesis in which the residual limb socket is horizontally anteriorly offset from the lower limb prosthesis and the residual limb socket is posteriorly to anteriorly inclined relative to the lower limb prosthesis comprising:

providing a coupler device comprising a coupler body having a top mounting surface including an aperture and a bottom mounting surface and having an anterior area and a posterior area;

said top mounting surface connecting said top mounting surface to said residual limb socket at a defined location on said top mounting surface;

said bottom mounting surface being adapted to connect said bottom mounting surface to said lower limb prosthesis at a defined location on said bottom mounting surface;

mounting the residual limb socket to the top mounting surface of said coupler;

mounting the lower limb prosthesis to the bottom mounting surface of said coupler so that a longitudinal centerline of the residual limb socket is horizontally offset posteriorly from a longitudinal centerline of the lower limb prosthesis a distance in the range of from about 0.5 to about 4.0 inches and the residual limb socket is inclined at an angle in the range of from about 5° to about 20° from posterior to anterior relative to said lower limb prosthesis; and disposing a locking mechanism having a toothed plunger including a pinion and a shaft within a transverse aperture of the coupler body;

inserting a pin comprising a shaft and a series of elevated rings along said shaft into the aperture on the top mounting surface;

intersecting said transverse aperture with said aperture of said top mounting surface when said pin is inserted; and rotating said pinion such that the pinion mates with said elevated rings of said pin and said pin is drawn into said body or exits said body.

36. A coupler device for connecting a residual limb socket to a lower limb prosthesis comprising:

a coupler body including a top mounting surface comprising an aperture sized to receive an alignment pin and a bushing, and a bottom mounting surface, said top mounting surface connecting said top mounting surface to a residual limb socket at a defined location on said top mounting surface;

said bottom mounting surface connecting said bottom mounting surface to said lower limb prosthesis at a defined location on said bottom mounting surface;

wherein said socket has a distal end and a proximal end and contains a sleeve having a distal end and a proximal end;

wherein said distal end of said sleeve houses a receptacle;

wherein said coupler body further comprises an aperture on the top mounting surface receiving an alignment pin and a bushing;

wherein said pin is sized for insertion into said receptacle, to pass through said aperture into said alignment bushing and pull said sleeve enclosed residuum into said socket and to further attach said sleeve to said coupler body; and wherein said distal end of said socket further includes an attachment ring that has an inner side and a keyway and said pin passes through said keyway to attach said sleeve to said coupler body.

* * * * *

UNITED STATES PATENT AND TRADEMARK OFFICE
CERTIFICATE OF CORRECTION

| | | |
|---|---|---|
| PATENT NO. | : 7,083,654 B2 | Page 1 of 1 |
| APPLICATION NO. | : 10/642047 | |
| DATED | : August 1, 2006 | |
| INVENTOR(S) | : Derek M. Helenberger et al. | |

It is certified that error appears in the above-identified patent and that said Letters Patent is hereby corrected as shown below:

Col. 12, line 22, claim 27, after "coupler" insert --device--.

Col. 12, line 39, claim 27, delete "surfaces." and insert therefor --surfaces,--.

Signed and Sealed this

Twenty-eighth Day of November, 2006

JON W. DUDAS
*Director of the United States Patent and Trademark Office*